(12) United States Patent
Roe

(10) Patent No.: US 6,911,912 B2
(45) Date of Patent: Jun. 28, 2005

(54) METHOD OF URINARY CONTINENCE TRAINING BASED ON AN OBJECTIVE MEASUREMENT OF THE BLADDER

(75) Inventor: Donald Carroll Roe, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 501 days.

(21) Appl. No.: 10/007,733

(22) Filed: Nov. 8, 2001

(65) Prior Publication Data

US 2003/0084906 A1 May 8, 2003

(51) Int. Cl.$^7$ .............................................. G08B 23/00
(52) U.S. Cl. ................................. 340/573.1; 600/449
(58) Field of Search ........................ 340/573.1, 573.5; 128/886; 600/438, 439, 443, 456, 449

(56) References Cited

U.S. PATENT DOCUMENTS

| | | | |
|---|---|---|---|
| 4,852,578 A | | 8/1989 | Companion et al. |
| 4,926,871 A | | 5/1990 | Ganguly et al. |
| 5,058,591 A | | 10/1991 | Companion et al. |
| 5,235,985 A | | 8/1993 | McMorrow et al. |
| 5,423,329 A | * | 6/1995 | Ergas .......................... 600/546 |
| 5,964,710 A | | 10/1999 | Ganguly et al. |
| 6,110,111 A | | 8/2000 | Barnard |
| 6,213,949 B1 | | 4/2001 | Ganguly et al. |

OTHER PUBLICATIONS

Forsythe, W.I. and Butler, R.J., "Fifty Years of Enuretic Alarms", *Archives of Disease in Childhood*, 1989, 64, 879–885.

Hansen, A.F., and Jorgensen, T.M., "Alarm Treatment: Influence on Functional Bladder Capacity", *Scand J. Urol Nephrol*, 1996, pp. 59–60, ISSN 0036–5599.

Bonde, H.V., et al., "Nocturnal Enuresis: Change of Nocturnal Voiding Pattern During Alarm Treatment", *Scand J. Urol Nephrol*, 28:349–352, 1994.

Petrican, P. and Sawan, M.A., "Design of a Miniaturized Ultrasonic Bladder Volume Monitor and Subsequent Preliminary Evaluation on 41 Enuretic Patients", *IEEE Transactions on Rehabilitation Engineering*, vol. 6, No. 1, Mar. 1988, pp. 66–74.

Beauchamp–Parent, A. and Sawan, M., "New Reconfigurable Ultrasonic Enuresis Monitoring System", *Proceedings of the 20th Annual International Conference of the IEEE Engineering in medicine and Biology Society*, vol. 20, No. 2, 1998, pp. 789–792.

Pretlow, R.A., "Treatment of Nocturnal Enuresis With An Ultrasound Bladder Volume Controlled Alarm Device", *The Journal of Urology*, vol. 162, 1224–1228, Sep. 1999.

* cited by examiner

*Primary Examiner*—Thomas Mullen
(74) *Attorney, Agent, or Firm*—Michael P. Hayden; Jay A. Krebs; Ken K. Patel

(57) ABSTRACT

Method of urinary continence training, utilizing an objective measurement, indicative of the state of fullness of the bladder of the subject, to identify the occurrence of an appropriate continence training opportunity. When the objective measurement equals or exceeds a signal threshold value, set to correspond to a bladder volume that is less than a reflexive urination volume, a signal is provided to the subject or to a caregiver. The objective measurement may be performed by a bladder monitor, using any of several modalities of automatic sensing, and preferably using ultrasound. The signal threshold value may be recalculated and increased, so as to continue to correspond to a relatively full bladder, as the subject grows and/or achieves progress toward continence. The method may include other steps directed to help the subject associate the physical sensation of a full bladder with voluntary urination, such as informing the subject that urination is imminent.

16 Claims, 10 Drawing Sheets

METHOD OF URINARY CONTINENCE TRAINING BASED ON AN OBJECTIVE MEASUREMENT OF THE BLADDER

FIELD OF THE INVENTION

This invention relates to a method of training a child to achieve urinary continence. The method utilizes an objective measurement indicative of the state of fullness of the bladder of the child to identify the occurrence of an appropriate continence training opportunity.

BACKGROUND OF THE INVENTION

Newborn babies are incontinent, i.e., they are unable to voluntarily retain their bodily discharges and, instead, urinate and defecate reflexively. As they mature physiologically, children typically achieve urinary and fecal continence, that is, they develop the ability to voluntarily retain their urine and feces. Coincident with the development of continence, children typically develop the ability to voluntarily urinate and defecate, and cease reflexive elimination. This development of continence and of voluntary elimination, in place of reflexive elimination, may be accelerated and/or guided by caregivers through associative and conditioning techniques of training the child. For the purpose of this invention, the term "continence training" is used to denote training for both continence, itself, and for the voluntary elimination that is associated with continence. Thus, the term "continence training" is synonymous with what is referred to as "toilet training" or "potty training", in some countries.

The methods of continence training of children vary widely between countries and cultures, and even within a given population. In certain cultures, the continence training is started at a relatively early age and involves intensive conditioning. For instance, continence training may begin prior to the child's first birthday, such as at 6 months of age or even earlier. The continence training methods used in these cultures are based on conditioning the child to eliminate waste upon some signal, whenever the caregiver perceives that the child needs to urinate or defecate. Such conditioning methods are often extremely time-consuming and require the caregiver to learn and detect subtle signals from the child related to potential urination and defecation. With respect to urinary continence training, such a conditioning method may ultimately lead to earlier association of the physical sensation of bladder "fullness" with the possibility of voluntary urination into the designated receptacle. However, since the caregiver does not know the state of the bladder, a significant amount of time is wasted, since the bladder is often not sufficiently full to require emptying, or to produce the desired physical sensation of fullness in the child, at the time at which the caregiver attempts the conditioning.

In other cultures, the continence training is started at a much later age, e.g., when the child demonstrates an interest in the achievement of continence, with the intention being to minimize the psychological stress on the child by waiting until the child shows an interest. In these cultures, the start of continence training is typically postponed until the child reaches about 18 to 24 months of age. As a result, many children in these cultures are not fully continence trained until age three or later, even though they are physiologically capable of achieving continence much earlier. In addition to increasing the cost of caring for the child, through necessitating the purchase of diapers, disposable training pants, etc., delayed continence training may also result in the child feeling low self-esteem, if his or her chronological peers are already continent, and may lead to issues with preschools or daycare facilities that require that children in their care are continent.

Many types of continence training methods and aids have been utilized, including progress charts, reward systems, urination "targets" for boys, electronic wetness alarms, progress scales, readiness questionnaires, and thermal and tactile training signals in disposable absorbent products, among many others. A key step in urinary continence training, in particular, is helping the child to learn to associate the physiological sensation of a "full" bladder with voluntary urination. The methods and aids described in the prior art fail to provide a direct link for the child, or the child via the caregiver, between this sensation and voluntary urination.

SUMMARY OF THE INVENTION

The present invention is directed to a method of training a child to achieve urinary continence and voluntary urination, in which an appropriate continence training opportunity is identified by obtaining an objective measurement indicative of the state of fullness of the child's bladder and providing a signal when the measurement reaches a threshold value that precedes reflexive urination.

DETAILED DESCRIPTION OF THE INVENTION

Figure 1:
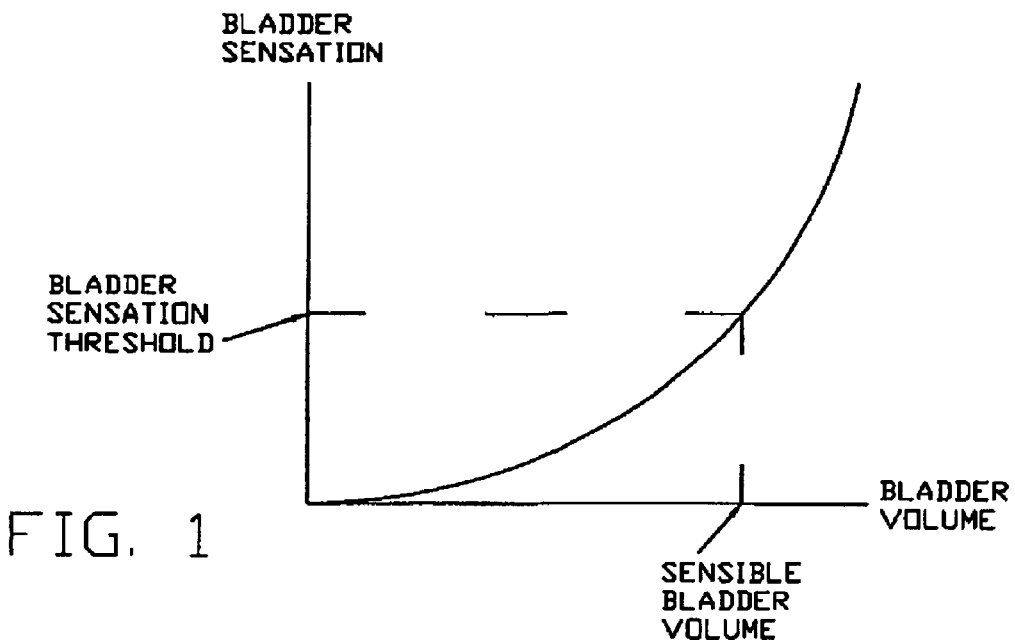
FIG. 1 shows the general relationship between the volume of urine in the bladder and the magnitude of the corresponding physical sensation associated with the distending bladder.

For the purposes of this invention, "continence training" is defined as the process by which a caregiver, such as a parent, helps an incontinent child achieve voluntary control over, and independent management of, the timing and location of his or her urination and defecation. Thus, in this context, continence training, "continence", and "continent", refer to the child's ability to voluntarily retain bodily discharges and to voluntarily release these bodily discharges at an appropriate time and place, preferably into a sanitary waste receptacle, such as a toilet fixture. Generally, continence is not achieved in a single step. Instead, continence training often includes one or more of a number of important intermediate milestones. For example, the ability of the child to tell the caregiver that he or she is ready to urinate and/or defecate, the ability to voluntarily retain waste while awake, and the ability to urinate and defecate only in the designated receptacle are all common intermediate milestones or successes on the path to full continence. The method of this invention is primarily concerned with, but not limited to, the achievement of urinary continence while awake.

The method of the present invention may provide the benefit of significantly earlier and/or less psychologically stressful achievement of urinary continence, at least while the child is awake. In general, the use of this method may enhance the effectiveness of any continence training regimen. In particular, this method may be used in conjunction with aspects of existing regimens, such as the use of progress charts and the like.

The achievement of urinary continence while awake may require both conditioning and the development of conscious awareness in the child of the physical sensation of a full or mostly full bladder. The method of this invention involves the identification of appropriate continence training opportunities, on which the caregiver can capitalize to help the child develop this conscious awareness. The term "appropriate", as used herein in relation to a continence training opportunity, refers to an occurrence or a condition that is especially suitable for use in training the child to achieve urinary continence, such as when the bladder contains a quantity of urine sufficient to, warrant urination. Thus, the urinary continence training method of the present invention includes the steps of obtaining an objective measurement that is indicative of the physical state of the bladder and providing a signal to the child and/or to the caregiver when the value of the measurement reaches some signal threshold value corresponding to a full or relatively full bladder. These steps are shown in the flow charts of FIG. 3, FIG. 4, FIG. 5, FIG. 6, FIG. 7, FIG. 8, FIG. 9, and FIG. 10.

The occurrence of this state of fullness of the bladder provides an appropriate opportunity to train the child to associate the physical sensation of a full or mostly full bladder with voluntary urination. By providing the signal based upon the objective measurement, this method can identity appropriate continence training opportunities to the caregiver, as shown in the flow charts of FIG. 8 and FIG. 10. Given this objective indication of relative bladder fullness, the caregiver may query the child about his or her perceived physical sensations as shown in the flow charts of FIG. 4, FIG. 5, and FIG. 6, inform the child that urination is possible or imminent as shown in the flow charts of FIG. 5 and FIG. 6, take the child to the desired location for urination, place the child in the proper position to urinate into the designated receptacle as shown in the flow charts of FIG. 6 and FIG. 9 encourage the child to attempt urination, or perform any number of other acts that help the child associate the physical sensation of the full bladder with voluntary urination. Since this method is based on an objective measurement and does not require the child to communicate bladder fullness or the caregiver to guess when a continence training opportunity exists, this method of continence training is applicable to incontinent children of any age in the ranges noted above, at which continence training is begun in various cultures.

Preferably, the signal threshold value is set such that it indicates a relatively full bladder containing less urine than in the state of fullness at which reflexive urination or other involuntary discharge of urine will occur. The term "reflexive" is used herein to refer to an action of the nervous system, below the level of consciousness, in which a muscular response to a stimulus is automatically effectuated. An example of an involuntary, but non-reflexive discharge of urine is that which may occur through leakage past the urinary sphincter due to excessive pressure. The volume of urine in the bladder at which the reflexive release of urine occurs is referred to herein as the "reflexive urination volume" of the bladder. The value of the objective measurement corresponding to the reflexive urination volume is referred to herein as the "reflexive urination level". This reflexive urination volume may be measured and used to determine the signal threshold value as shown in the flow charts of FIG. 3, FIG. 4, FIG. 5, FIG. 6, FIG. 7, FIG. 8, FIG. 9, and FIG. 10. Since the reflexive urination volume varies somewhat between different urination events, an average of the reflexive urination volume or of the corresponding reflexive urination level may be used to determine the signal threshold value. Alternatively, the lowest or highest observed reflexive urination volume, another empirically derived value, or even an arbitrary value, may be used to determine the signal threshold value. For example, the signal threshold value may be set to correspond to an average of the daytime urination volume.

Various methods may be used to determine the urination volume of interest. These methods may include regular or random sampling of the volume of urine retained in a diaper or other article worn by the incontinent child. Typically, the dry and wet weights of a diaper may be compared, and the fact that the specific gravity of urine is approximately equal to one may be used in order to estimate the volume of urine retained in the diaper. As an example of an alternative method, the volume of urine in the bladder may be regularly or randomly measured until sufficient data are collected to make practical an estimation of the reflexive urination volume. Similarly, in accordance with the concept introduced above and applied throughout this description, an indirect parameter, such as the reflexive urination level, may be used in lieu of a direct determination of a volume of interest. Of course, a bladder monitor as described herein may be used to determine the urination volume of interest. For example, the bladder monitor may be used to track the child's bladder volume, or other objective measurement indicative of the physical state of the bladder, over one or more one time periods during which at least one urination, and preferably at least several urinations occur. The local maximum of the bladder volume or other objective measurement prior to a significant decrease in the same parameter generally corresponds to the child's urination event and, therefore, to the reflexive urination volume or level, respectively.

Ideally, the signal threshold value should be set high enough to correspond to a bladder volume at which a discernible physical sensation may be produced by a filling bladder, but low enough that reflexive urination does not occur prior to a signal indicating a continence training opportunity. In any case, the signal threshold value should be set high enough that the child is likely to experience the physical sensation of bladder fullness at the time that the signal is provided. Setting the signal threshold value at this level will help to ensure that the opportunity is provided for the child to associate this sensation with the subsequent act of urination or with the possibility to urinate. Typically, the signal threshold value is set to correspond to a specific percentage or proportion of one of the previously mentioned reflexive urination volumes. In certain preferred embodiments of the method of the present invention, the signal threshold value is set to correspond to a bladder volume that is about 90% or less of the selected reflexive urination volume. In alternate preferred embodiments, the signal threshold value is set to correspond to a bladder volume that is about 80% or less of the selected reflexive urination volume. In further embodiments, the signal threshold value is set to correspond to a bladder volume that is about 70% or less of the selected reflexive urination volume.

FIG. 1 depicts the general relationship between the volume of urine in the bladder, designated "bladder volume", and the magnitude of the corresponding physical sensation, designated "bladder sensation", which is associated with the distending bladder. As an individual's bladder begins to fill, it initially expands with very little increase in internal pressure and with the physical sensation at a level that is too low to be discernible by the individual. As the bladder continues to fill, the internal pressure and the magnitude of the physical sensation increase until the physical sensation eventually becomes discernible by the individual. At this point of potential discernment of the physical sensation, the opportunity is presented for the individual to become consciously aware of the sensation. The "bladder sensation threshold" shown in FIG. 1 represents a magnitude of the physical sensation at which a hypothetical, but representative, individual, such as a child, may become consciously aware of the physical sensation of the fullness of the bladder.

The bladder volume at which the bladder sensation reaches the bladder sensation threshold is designated the "sensible bladder volume" for the individual. The sensible bladder volume is generally less than the bladder volume at which either voluntary or reflexive urination typically occurs for the individual. Not all individuals will initially be consciously aware of the physical sensation associated with the increase in the bladder volume. In these cases, the sensible bladder volume is the bladder volume for which the individual has the potential of consciously discerning the nerve signals associated with bladder fullness, after proper training or conditioning. Also, the onset of discernible sensation may be gradual over a range of bladder volume. In the case of such a gradual onset, the bladder sensation threshold may correspond to a range of bladder volume rather than to a discrete value. However, a point on the curve is shown in this example, to illustrate the principle involved. The bladder sensation threshold, and therefore the sensible bladder volume, may change over time as the individual grows and/or gains increasing control over his or her urinary functions. Preferably, the reflexive urination volume increases over time in conjunction with, or as a result of, the continence training as described herein, thereby increasing the difference between the sensible bladder volume and the reflexive urination volume. Such an increase in the reflexive urination volume may effectively provide more time for the child to move to the location of the designated receptacle and voluntarily urinate, and thus avoid reflexive urination.

Figure 2:
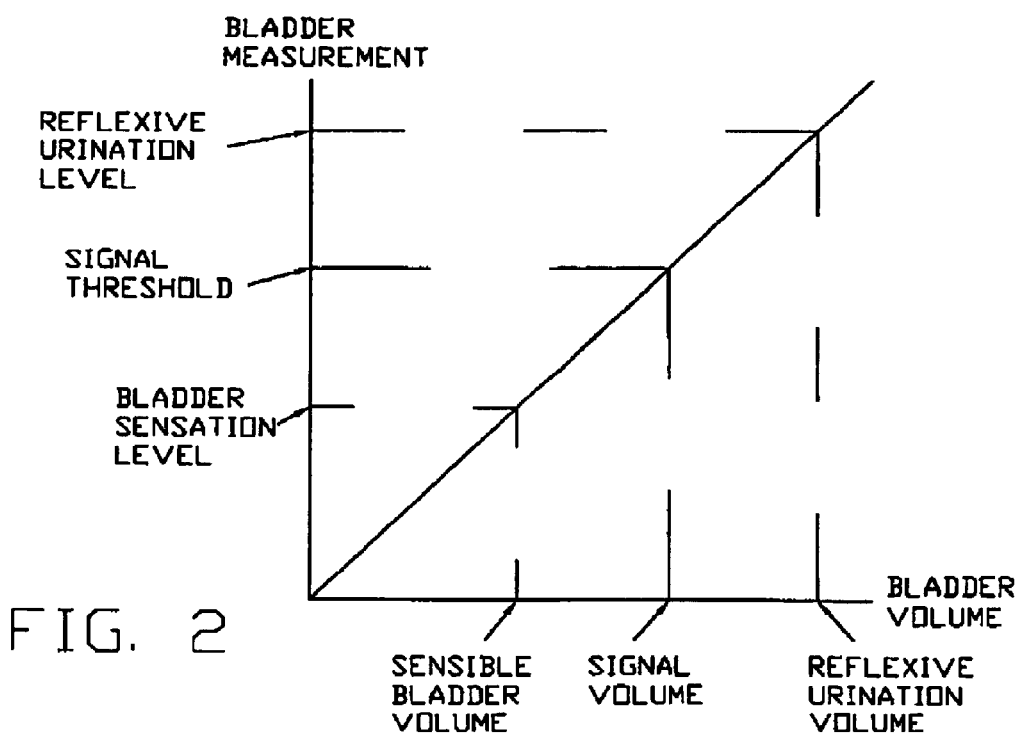
FIG. 2 shows the general relationship between a representative objective measurement that is indicative of the physical state of the bladder and the volume of the bladder.
Figure 3:
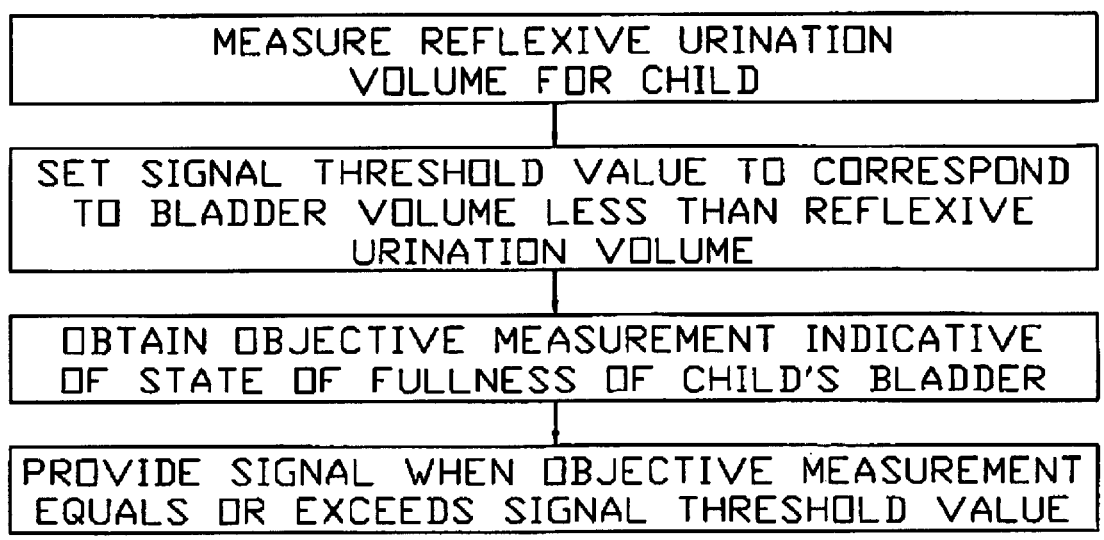
FIG. 3 shows a flow chart for a urinary continence training method of the present invention.
Figure 4:
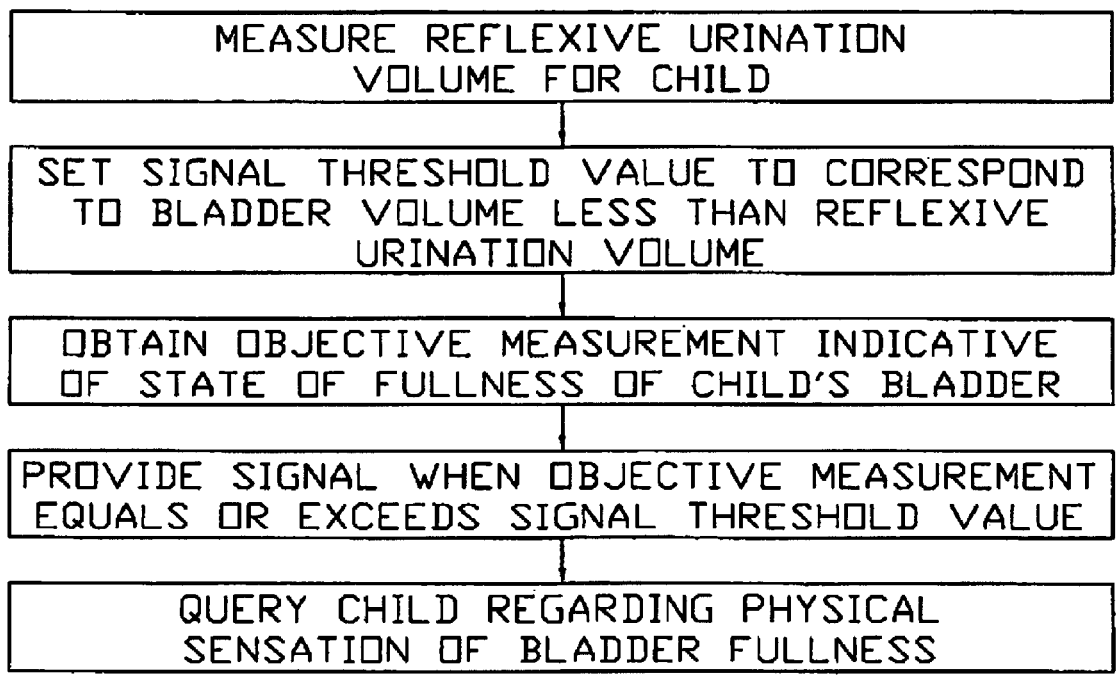
FIG. 4 shows a flow chart for a urinary continence training method of the present invention.
Figure 5:
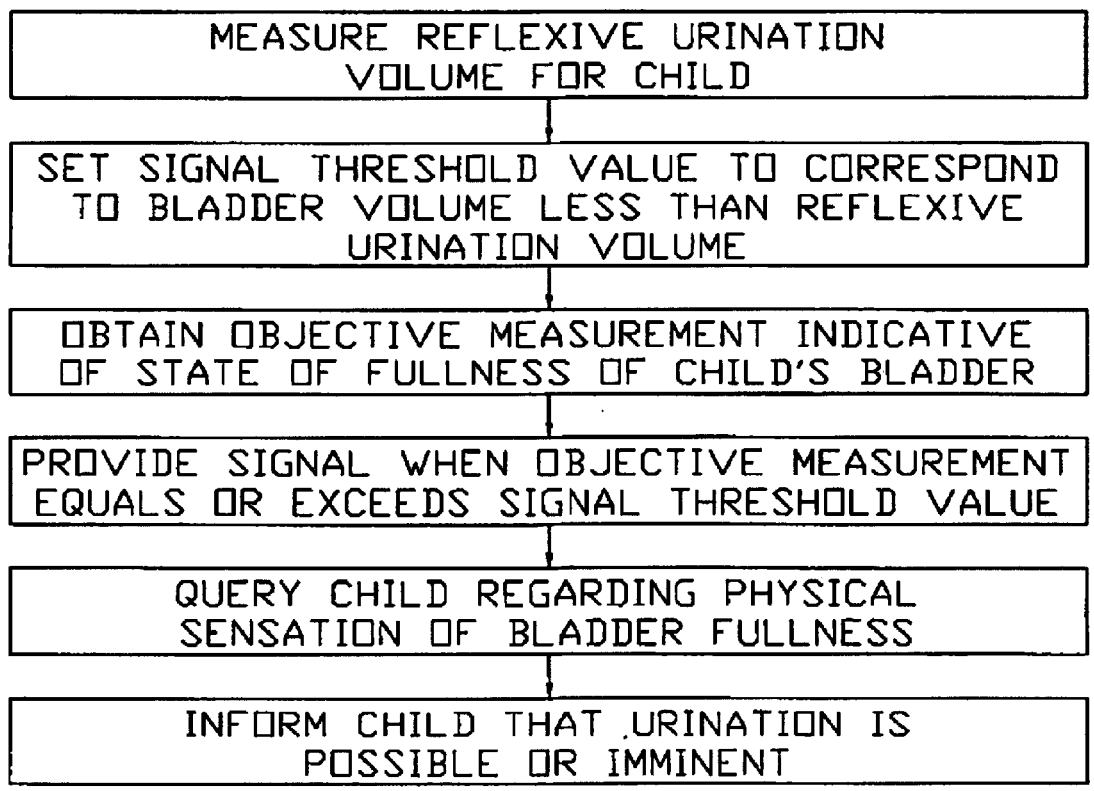
FIG. 5 shows a flow chart for a urinary continence training method of the present invention.
Figure 6:
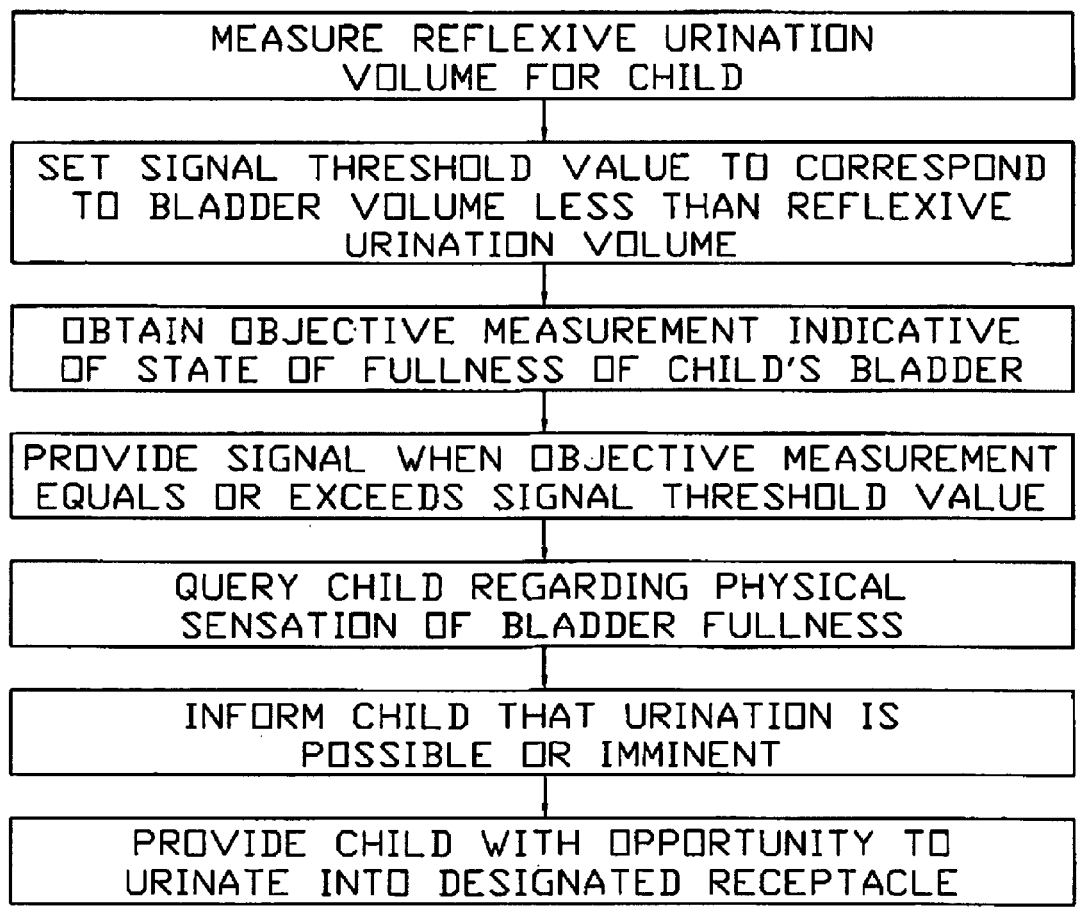
FIG. 6 shows a flow chart for a urinary continence training method of the present invention.

FIG. 2 depicts a representative objective measurement that is indicative of the physical state of the bladder, as a function of the bladder volume. In order to facilitate the effective association between discernible, or potentially discernible, bladder sensation and the physical possibility of urination, a signal is provided at a bladder volume that is greater than the sensible bladder volume, but less than the selected reflexive urination volume. This intermediate bladder volume, corresponding to the signal threshold value of the objective measurement, is designated the "signal volume" of the bladder. Also, the value of the objective measurement corresponding to the sensible volume of the bladder is designated the "bladder sensation level". Accordingly, the signal threshold is set at a value of the bladder measurement between the bladder sensation level and the reflexive urination level.

In certain preferred embodiments, the method of urinary continence training also includes the ongoing or occasional monitoring of the reflexive urination volume after the threshold value is initially set. As the child grows and as progress toward continence is achieved, the bladder often increases in maximum capacity. This monitoring may provide a basis for the assessment of continence training progress. Also, if the reflexive urination volume increases, the threshold value may be recalculated and increased so as to continue to correspond to a relatively full bladder. Alternatively, the threshold value may be automatically recalculated by a measurement device, such as a bladder monitor, as described below.

The objective measurement indicative of the physical state of the bladder may be a measurement of the bladder volume, either estimated, measured, or calculated via an algorithm. Also, the objective measurement may be a measurement of a dimension of the bladder, a cross-sectional area of the bladder, and/or of the bladder shape. Likewise, the objective measurement may be a measurement indicating the presence of the bladder in a specific region of the abdomen, since the bladder tends to move as it fills and expands. Similarly, the distention of the bladder, the tension in the bladder walls, the electrical activity in the muscles or nerves surrounding the bladder, the optical properties of the bladder, the acoustic properties of the bladder, the compression of the tissues surrounding the bladder, or the distention of the skin in the region of the abdomen containing the bladder, or any other measurable physical change in the child's anatomy that is related to or correlatable with an increase in urine volume in the child's bladder, may be objectively measured in order to ascertain the state of fullness of the bladder. In general, the objective measurement may be any measurement that can be correlated to one or more of the aforementioned parameters that are indicative of the state of fullness of the bladder. The objective measurement of the state of fullness of the bladder may employ any modality of automatic sensing known in the art, including ultrasound, audible sound, light (including coherent light), infrared radiation, active or passive electrical properties, including EMG signals and electrical impedance measurements, and the like. The employed modality is preferably non-invasive.

Preferably, the measurement of the state of fullness of the bladder in the method of the present invention utilizes ultrasound to provide a measurement or empirical indication or estimate of the bladder dimensions, cross-sectional area, and/or volume of the bladder. In certain alternative preferred embodiments, ultrasound is used to measure the distention of, or tension in, the walls of the bladder, the blood flow in the bladder walls, vibration in the bladder walls, or the acoustic transmission properties of the tissues surrounding the bladder, which are affected by the relative compression of the tissues that are displaced as the bladder distends during filling.

Figure 7:
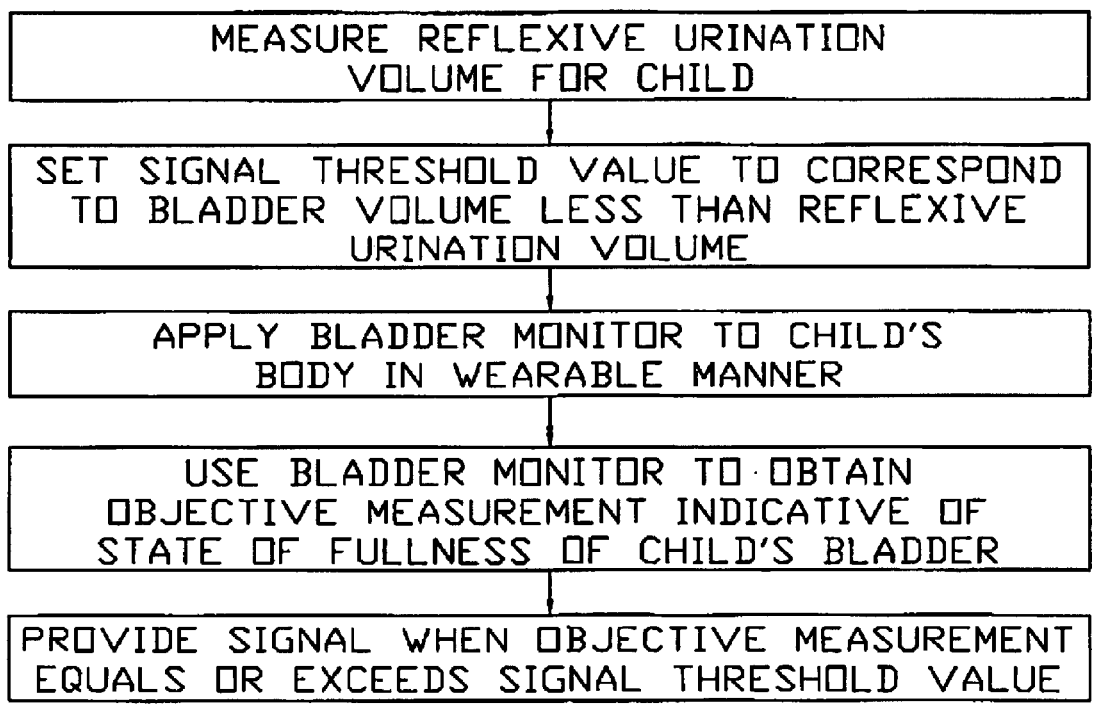
FIG. 7 shows a flow chart for a urinary continence training method of the present invention.
Figure 8:
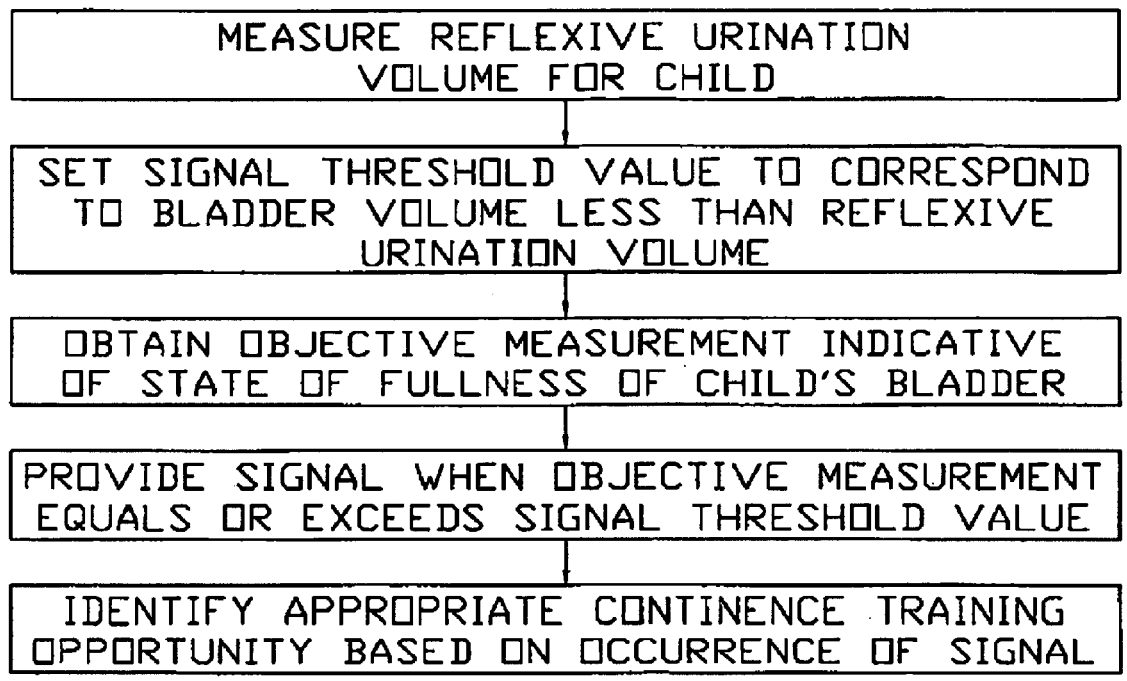
FIG. 8 shows a flow chart for a urinary continence training method of the present invention.
Figure 9:
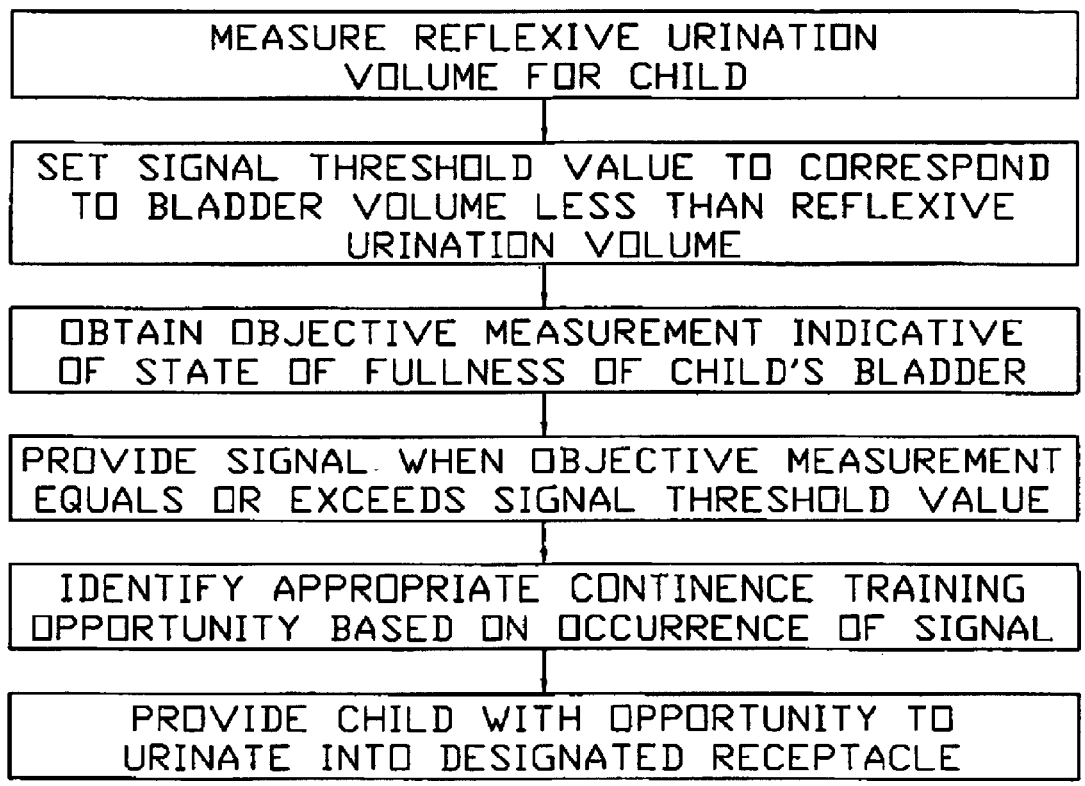
FIG. 9 shows a flow chart for a urinary continence training method of the present invention.
Figure 10:
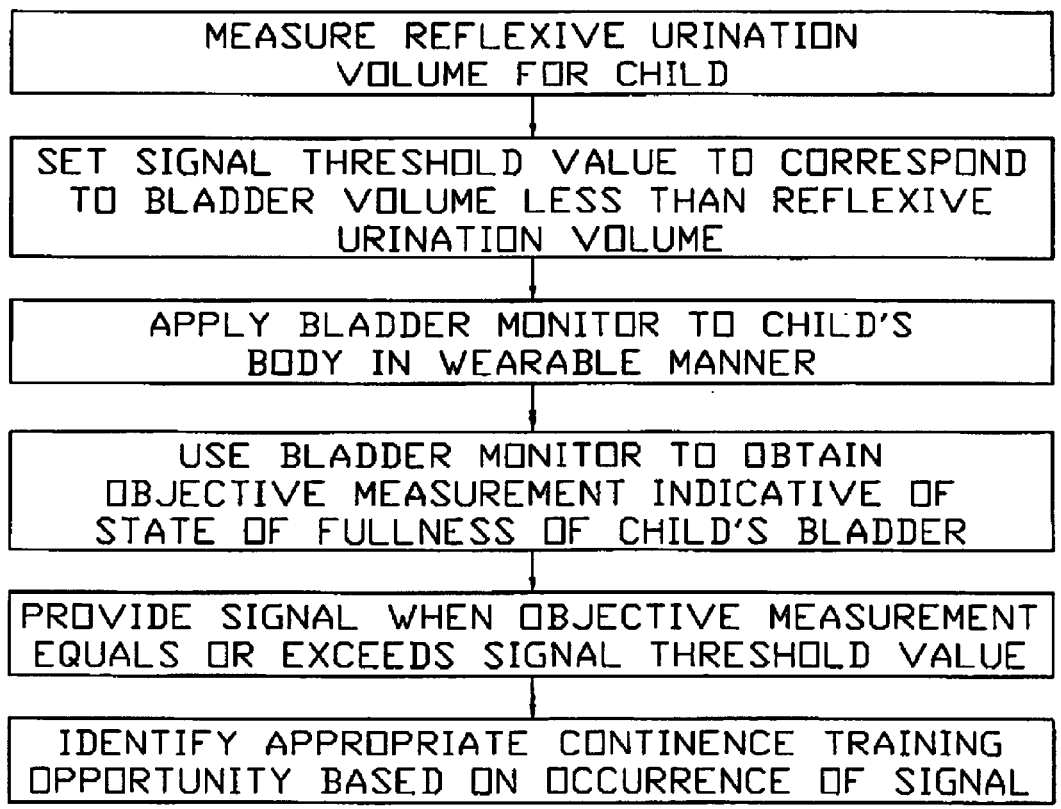
FIG. 10 shows a flow chart for a urinary continence training method of the present invention.

Preferably, the measurements indicative of the state of fullness of the bladder are performed by a bladder volume monitor or "bladder monitor" as shown in the flow charts of FIG. 7 and FIG. 10. A bladder monitor utilizing ultrasound may generally comprise one or more ultrasonic transducers adapted to send pulsed ultrasonic energy into the child's abdomen and to receive reflections of this energy. The bladder monitor also preferably includes the necessary software to generate a measurement of the bladder state on the bank of the reflected ultrasonic energy and to compare it to a threshold value. The bladder monitor also preferably includes one or more mechanisms to provide a signal or an alarm to the child and/or to the caregiver when the bladder signal reaches the threshold value. The signal or alarm may be provided in any useful form, such as an audible alarm, a tactile alarm, a visible alarm, and the like.

Additionally, the bladder monitor preferably includes a mechanism to calibrate the monitor and/or to reset the signal threshold value, and the electronics and power source to support the system. Preferably, the monitor may be calibrated and the signal threshold value may be reset automatically or upon the intervention of the caregiver. Similarly, the type and intensity of the alarm, as well as the direction of the alarm to the child or to the caregiver, may preferably be changed by the caregiver. For example, if the child fails to respond to the signal within a set amount of time, or if several potential continence training opportunities are missed because the child urinates before action can be taken by the caregiver, these parameters may be changed in order to better capitalize on the potential opportunities. Optional components of a bladder monitor include a display, a data storage and analysis mechanism, a telemetry system, a remote caregiver alarm unit, and one or more mechanisms to secure the monitor to the child or to a supporting garment. For example, the bladder monitor may have the capability to store data that are useful for the tracking and assessment of progress toward the achievement of urinary continence.

The bladder monitor used in the method of the present invention may be a handheld unit or may comprise a wearable device. As used herein, the term "wearable" refers to the adaptability of the monitor, or a portion thereof, to be applied to a child's body for the duration of his or her normal activities without substantially limiting these activities as shown in the flow charts of FIG. 7 and FIG. 10. The scope of this term includes the association with, or incorporation into, a garment, the partial or full encirclement of at least a portion of the subject's anatomy, the adhesive application to the child's skin, or the design of the device to simulate a garment, belt, or any other known wearable garment. Wearable devices or components may include elastic and other belts, disposable or durable clothing, disposable absorbent articles such as diapers, disposable waste-receiving articles such as adhesively or releasably attachable strips such as bandages and diagnostic strips, adhesively attached devices, and other wearable items known in the art. Additionally, the device, or a component thereof, may be releasably affixed to any of the above wearable articles or to any other carrier structure that may be attached to the subject or to a wearable article.

For example, the bladder monitor may comprise an ultrasonic transducer affixed adhesively to the subject's lower abdominal skin and connected by wire to a closed housing containing the bladder monitor electronics and power supply, which may be affixed to one of the subject's garments. Alternatively, the bladder monitor may comprise an ultrasonic transducer integrated into a housing and the housing may be formed as, or incorporated into, a belt that may be applied around the subject's lower abdomen. In any case, the ultrasonic transducer must be held in intimate contact with the subject's skin in the vicinity of the lower abdominal area between the navel and the pubic bone.

Suitable bladder monitors, ultrasonic devices, and approaches to obtain objective measurements of the physical state of the bladder are described in U.S. Pat. Nos. 4,926,871; 5,964,710; 5,235,985; 5,058,591; 4,852,578; 5,195,521; 6,213,949, and 6,110,111, and in the co-pending and commonly assigned U.S. patent application Ser. No. 09/643,008, the relevant portions of the disclosures of which are incorporated herein by reference. Exemplary bladder monitors are also described in the scientific literature, such as Pretlow, R. A., "Treatment of Nocturnal Enuresis With an Ultrasound Bladder Volume Controlled Device", The Journal of Urology, Vol. 162, pp. 1224–1228, September, 1999; Beauchamp-Parent, A., et al, "New Reconfigurable Ultrasonic Enuresis Monitoring System", Proceedings of the $20^{th}$ Annual International Conference of the IEEE Engineering in Medicine and Biology Society, Vol. 20, No. 2, pp. 789–792, 1998, and Petrican, P. et al, "Design of a Miniaturized Ultrasonic Bladder Volume Monitor and Subsequent Preliminary Evaluation on 41 Enuretic Patients" IEEE Transactions on Rehabilitation Engineering, Vol. 6, No. 1, pp. 66–74, March 1998, the relevant portions of which are incorporated herein by reference.

Several of the devices and approaches in the references mentioned above have been developed to address the needs of children experiencing nocturnal enuresis, which is the involuntary release of urine during sleep by otherwise continent children. Nocturnal enuresis is generally a medical condition and may be caused by physical or biochemical abnormalities, sleeping too deeply, environmental or psychological trauma, and the like. The general approach directed to nocturnal enuresis is to attempt to teach the child to awaken prior to urination and/or to increase the size of the child's bladder.

The urinary continence training method of the present invention is significantly different from those methods directed to nocturnal enuresis, in that the present method is directed to training incontinent children to achieve urinary continence while awake, rather than while asleep. These children are typically completely incontinent at the start of the training and must be taught the relationship between the physical sensations related to bladder fullness and voluntary urination. The bladder monitor used in this method provides an indication that a child, who is in the earliest stages of continence training, is at a "teachable" point, i.e., that an appropriate continence training opportunity exists, and that it is appropriate to take the child to the toilet, or other appropriate urination location, in the near future, since the child is almost ready to urinate. The accurate identification of appropriate continence training opportunities in the present method significantly increases the continence training success rate and helps to eliminate abortive attempts to train the child, when the child is not ready to urinate. Thus, the present method also reduces the psychological stress associated with such failed continence training attempts. As the child progresses toward continence, the bladder monitor may be configured to remind the child that urination is imminent, in case the child is preoccupied at the time and fails to notice the physical sensation of the gradual increase in the bladder volume.

The measurements of the bladder state may be performed continuously or intermittently. Intermittent measurements may be performed automatically, at some preset or programmable interval driven by the bladder monitor electronics, or manually by the caregiver. Preferably, the measurements are made automatically at intervals of between about 5 seconds and about 10 minutes. More typically, the measurements are automatically made at intervals of between about 2 minutes and about 8 minutes. The measurements may be done on an ongoing basis, e.g., while the child wears a bladder monitor for significant blocks of time as he or she engages in his or her normal activities, or during specific periods of time that the caregiver designates as continence training periods.

Figure 11:
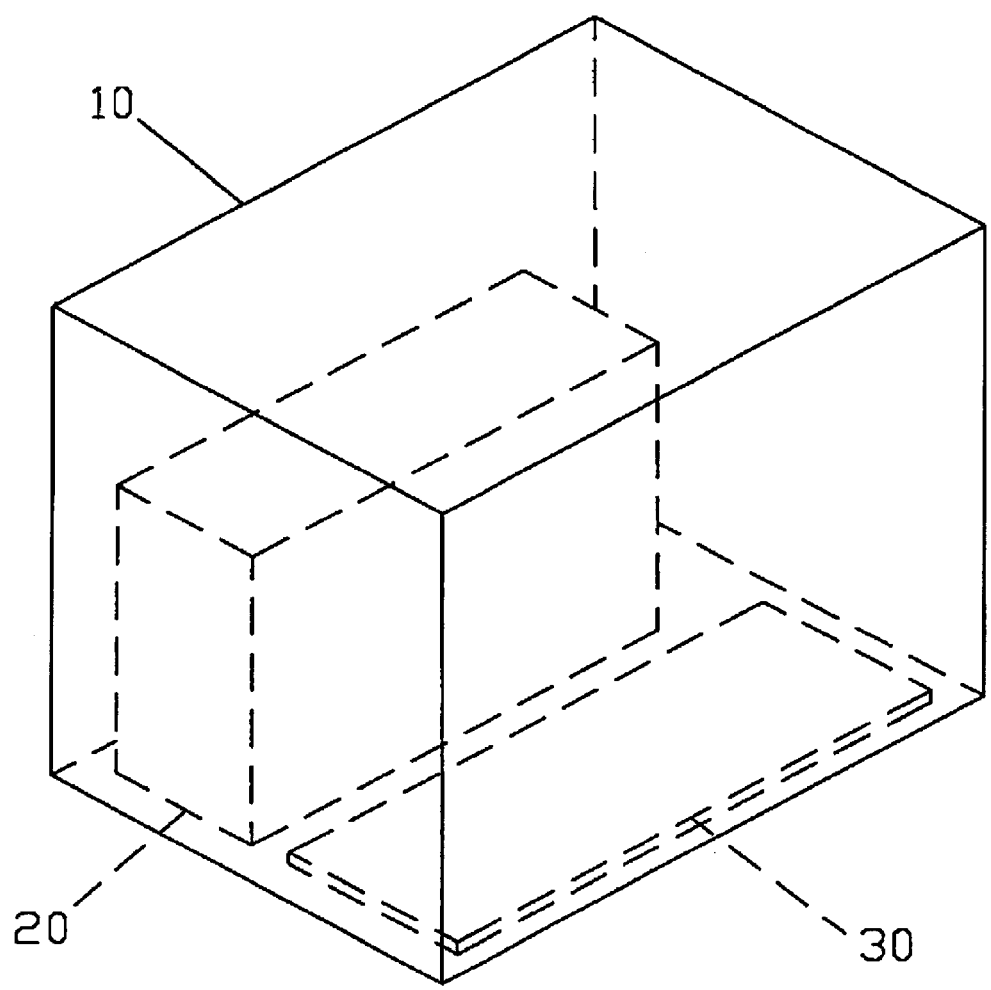
FIG. 11 shows a package containing a bladder monitor and instructions.

A packaged article of commerce may be useful in relation to the method of the present invention. Such an article of commerce may comprise, for example, a package including a bladder monitor and instructions for using the bladder monitor to perform the method of continence training described herein. Such a package 10 containing a bladder monitor 20 and instructions 30 is shown in FIG. 11. The term "instructions" refers herein to an outline or manual of technical procedure. In general, the instructions may describe the use of the bladder monitor for any of the steps for which it can be used, as well as describing associated steps of the method. For example, the instructions may describe any of the steps mentioned, including those of using the bladder monitor to obtain the objective measurement, providing a signal when the measurement equals or exceeds a signal threshold value, and identifying an appropriate continence training opportunity based on the occurrence of the signal. The instructions may, likewise, describe other steps, including those of using the bladder monitor to measure the reflexive urination volume and setting the signal threshold value to correspond to a bladder volume that is less than the reflexive urination volume, for example.

The descriptive nature of the instructions may be provided by text, by figures or diagrams, or by any other visual guide, such as by the sequential numbering of operations or of operable devices in correspondence with an effective sequence of steps of the method of the present invention. Also, the instructions may be included with the package in any of several forms. For example, the instructions may be printed on the outside or the inside of the package, itself, or may be in the form of a sheet or card contained inside the package or attached to the package. In some embodiments, the instructions may form part of the physical embodiment of the bladder monitor as, for instance, when the instructions are engraved on, or affixed to, the bladder monitor. In general, the instructions may be provided in any form in which the functional relationship between the instructions and the use of the bladder monitor in the method of continence training is clear to the user.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention.

What is claimed is:

1. A method for training a child to achieve urinary continence by identifying an appropriate continence training opportunity, comprising the steps of:
   measuring a reflexive urination volume for the child;
   setting a signal threshold value to correspond to a bladder volume that is less than the reflexive urination volume;
   obtaining an objective measurement indicative of a state of fullness of the child's bladder; and
   providing a signal to the child or to a caregiver when the measurement equals or exceeds the signal threshold value.

2. The method of claim 1 further comprising the step of querying the child regarding his or her physical sensation of bladder fullness.

3. The method of claim 2 further comprising the step of informing the child that urination is possible or imminent.

4. The method of claim 3 further comprising the step of providing the child with the opportunity to urinate into a designated receptacle.

5. The method of claim 1 wherein the objective measurement correlates to a dimension of the bladder, a cross-sectional area of the bladder, or a volume of the bladder.

6. The method of claim 1 wherein the signal is an audible alarm, a tactile alarm, or a visible alarm.

7. The method of claim 1 including using a bladder monitor to obtain the objective measurement.

8. The method of claim 1 including utilizing ultrasound to obtain the objective measurement.

9. The method of claim 1 further comprising the steps of applying a bladder monitor to the child's body in a wearable manner and using the bladder monitor to obtain the objective measurement.

10. A method for training a child to achieve urinary continence, comprising the stops of:
    measuring a reflexive urination volume far the child;
    setting a signal threshold value to correspond to a bladder volume that is less than the reflexive urination volume;
    obtaining an objective measurement indicative of a state of fullness of the child's bladder;
    providing a signal to the child or to a caregiver when the measurement equals or exceeds the signal threshold value; and
    identifying an appropriate continence training opportunity based on an occurrence of the signal.

11. The method of claim 10 further comprising the step of providing the child with the opportunity to urinate into a designated receptacle.

12. The method of claim 10 wherein the objective measurement correlates to a dimension of the bladder, a cross-sectional area of the bladder, or a volume of the bladder.

13. The method of claim 10 wherein the objective measurement is obtained during a specific period of time that the caregiver designates as a continence training period.

14. The method of claim 10 including using a bladder monitor to obtain the objective measurement.

15. The method of claim 10 further comprising the steps of applying a bladder monitor to the child's body in a wearable manner and using the bladder monitor to obtain the objective measurement.

16. An article of commerce comprising a package including:
    a bladder monitor adapted to perform an objective measurement indicative of a state of fullness of a child's bladder and provide a signal to the child or to a caregiver when the measurement equals or exceeds a signal threshold value; and
    instructions for a user of the article for training the child to achieve urinary continence by performing the steps of measuring a reflexive urination volume for the child, setting the signal threshold value to correspond to a bladder volume that is less than the reflexive urination volume, using the bladder monitor to obtain the objective measurement, and identifying an appropriate continence training opportunity based on an occurrence of the signal.

* * * * *

UNITED STATES PATENT AND TRADEMARK OFFICE
CERTIFICATE OF CORRECTION

PATENT NO.        : 6,911,912 B2
APPLICATION NO. : 10/007733
DATED             : June 28, 2005
INVENTOR(S)       : Donald Carroll Roe It is certified that error appears in the above-identified patent and that said Letters Patent is hereby corrected as shown below:

<u>Column 3</u>

Line 32, delete "to," and insert -- to --.

Line 47, delete "identity" and insert -- identify --.

<u>Column 7</u>

Line 4, delete "bank" and insert -- basis --.

<u>Column 10</u>

Line 20, delete "stops" and insert -- steps --.

Line 21, delete "far" and insert -- for --.

Signed and Sealed this

Eighteenth Day of December, 2007

JON W. DUDAS
*Director of the United States Patent and Trademark Office*